United States Patent
Du

(10) Patent No.: US 10,318,147 B2
(45) Date of Patent: Jun. 11, 2019

(54) METHOD AND SYSTEM OF GESTURE RECOGNITION IN TOUCH DISPLAY DEVICE

(71) Applicant: Shenzhen China Star Optoelectronics Technology Co., Ltd., Shenzhen, Guangdong (CN)

(72) Inventor: Peng Du, Guangdong (CN)

(73) Assignee: SHENZHEN CHINA STAR OPTOELECTRONICS TECHNOLOGY CO., LTD., Shenzhen (CN)

( * ) Notice: Subject to any disclaimer, the term of this patent is extended or adjusted under 35 U.S.C. 154(b) by 204 days.

(21) Appl. No.: 14/785,937

(22) PCT Filed: Jul. 20, 2015

(86) PCT No.: PCT/CN2015/084458
§ 371 (c)(1),
(2) Date: Dec. 6, 2016

(87) PCT Pub. No.: WO2016/201760
PCT Pub. Date: Dec. 22, 2016

(65) Prior Publication Data
US 2017/0153805 A1    Jun. 1, 2017

(30) Foreign Application Priority Data
Jun. 17, 2015 (CN) .......................... 2015 1 0337013

(51) Int. Cl.
*G06F 3/041* (2006.01)
*G06F 3/0488* (2013.01)
(Continued)

(52) U.S. Cl.
CPC ........ *G06F 3/04883* (2013.01); *G06F 3/0237* (2013.01); *G06F 3/0488* (2013.01);
(Continued)

(58) Field of Classification Search
CPC .. G06F 3/0488; G06F 3/04883; G06F 3/0237; G06F 2203/04104
See application file for complete search history.

(56) References Cited

U.S. PATENT DOCUMENTS 8,327,295 B2 * 12/2012 Ikeda .................. G06F 3/04883
382/179
2010/0005428 A1 * 1/2010 Ikeda .................. G06F 3/04883
715/863
2010/0259493 A1    10/2010 Chang et al.

FOREIGN PATENT DOCUMENTS

CN    101620511 A    1/2010
CN    101859226 A    10/2010
(Continued)

OTHER PUBLICATIONS

International Search Report dated Jul. 20, 2015 for International Patent Application No. PCT/CN2015/084458.
(Continued)

*Primary Examiner* — Vijay Shankar

(57) ABSTRACT

Disclosed is a method and system of gesture recognition in a touch display device, which is able to predetermine gesture inputs possibly to be made by a user prior to the completion of the user's touch input, and enable a display unit to display all possible similar gesture inputs so as to provide an instruction (or navigation guidance) for the user. Thus, when using a large-sized touch display device, the user does not have to perform touch operations widely throughout the screen of the display device, because the system can recognize the similar gesture inputs in advance, which renders it easier for the user to operate on the touch display device, thereby obtaining a better user experience.

8 Claims, 2 Drawing Sheets

(51) Int. Cl.
  *G06F 9/38* (2018.01)
  *G06F 3/023* (2006.01)
  *G06F 19/00* (2018.01)

(52) U.S. Cl.
  CPC .......... *G06F 9/3806* (2013.01); *G06F 9/3832* (2013.01); *G06F 9/3844* (2013.01); *G06F 9/3846* (2013.01); *G06F 9/3848* (2013.01); *G06F 9/3861* (2013.01); *G06F 19/702* (2013.01); *G06F 19/704* (2013.01); *G06F 2203/04104* (2013.01); *G06F 2209/5019* (2013.01)

(56) References Cited

FOREIGN PATENT DOCUMENTS

| | | |
|---|---|---|
| CN | 102289341 A | 12/2011 |
| CN | 102298485 A | 12/2011 |
| CN | 102609165 A | 7/2012 |
| CN | 104020989 A | 9/2014 |
| EP | 2107448 A2 | 10/2009 |
| EP | 2369446 A2 | 9/2011 |
| JP | 5931627 B2 | 6/2016 |

OTHER PUBLICATIONS

Chinese Office Action dated Jun. 19, 2017 for Chinese Patent Application No. 201510337013.2.
Chinese Office Action dated Mar. 12, 2018 for Chinese Patent Application No. 201510337013.2.

* cited by examiner

METHOD AND SYSTEM OF GESTURE RECOGNITION IN TOUCH DISPLAY DEVICE

CROSS-REFERENCE TO RELATED APPLICATIONS

The present application claims benefit of Chinese patent application CN201510337013.2, entitled "Method and system of gesture recognition in touch display device" and filed on Jun. 17, 2015, the entirety of which is incorporated herein by reference.

TECHNICAL FIELD

The present disclosure relates to human-machine interaction technologies, and in particular, to a method and system of gesture recognition in a touch display device.

TECHNICAL BACKGROUND

Currently, touch display devices have been widely used on many occasions and fields as input devices substituting for or supplementing commonly used keyboards and mouse devices. With the production of a new generation of touch display devices supportive of multi-point touch interaction, great changes have taken place in applications of touch display devices. Touch display devices are now able to provide users with more interactions in more natural ways.

For existing touch display devices, especially those large-sized (e.g., 55-110 inches) ones, only after a user has finished the touch operation, the system of the touch display device is able to recognize a gesture input based on a received trajectory of the touch input and then execute a function corresponding to the gesture input. Due to the large size of these touch display devices, when performing a touch operation, the user has to move widely throughout the touch display device, i.e., move his or her finger(s) or a touch input device (e.g., a stylus) widely across the screen, so as to activate a desired function. This results in the user's fatigue and a disagreeable user experience.

SUMMARY OF THE INVENTION

The objective of the present disclosure is to provide a method of gesture recognition in a touch display device for allaying users' fatigue when using large-sized touch display devices, so as to provide a pleasant user experience.

In order to achieve the above objective, the embodiments of the present disclosure first provide a method of gesture recognition in a touch display device. The method comprises steps of: receiving a trajectory of a touch input on the touch display device in real time; recognizing and displaying all gesture inputs that match the currently received trajectory of the touch input prior to completion of the touch input; and receiving a gesture input determined from all the gesture inputs, and executing a function corresponding to said gesture input.

Preferably, in the step of recognizing all the gesture inputs that match the currently received trajectory of the touch input, features of the trajectory of the touch input are determined, and all the gesture inputs having said features are selected from a plurality of pre-stored gesture inputs.

Preferably, the features of the trajectory of the touch input include number of touch points, type of the trajectory, and quadrant where the trajectory is.

Preferably, when a real-time distance between two touch points of the touch input reaches a first preset distance, all the gesture inputs that match the currently received trajectory of the touch input are recognized and displayed.

Preferably, when distance variation of the trajectory of at least one of the touch points of the touch input reaches a second preset distance, all the gesture inputs that match the currently received trajectory of the touch input are recognized and displayed.

Preferably, when a time calculated from the beginning of the touch input reaches a preset time, all the gesture inputs that match the currently received trajectory of the touch input are recognized and displayed.

According to another aspect of the present disclosure, a system of gesture recognition in a touch display device is provided. The system comprises: a receiving unit, for receiving a trajectory of a touch input on the touch display device in real time; a recognizing unit, for recognizing all gesture inputs that match the currently received trajectory of the touch input prior to completion of the touch input; and an execution unit, for receiving a gesture input determined from all the gesture inputs displayed on the touch display device, and executing a function corresponding to said gesture input.

Preferably, the recognizing unit is further used to determine features of the trajectory of the touch input, and select all the gesture inputs having said features from a plurality of pre-stored gesture inputs.

Preferably, the features of the trajectory of the touch input include number of touch points, type of the trajectory, and quadrant where the trajectory is.

Preferably, the system further comprises a trajectory calculation unit for calculating a real-time distance between two touch points of the touch input. When the real-time distance between the two touch points calculated by the trajectory calculation unit reaches a first preset distance, the recognizing unit recognizes all the gesture inputs that match the currently received trajectory of the touch input.

Preferably, the trajectory calculation unit is further used to calculate distance variation of the trajectory of at least one of the touch points of the touch input. When the distance variation of the trajectory of the at least one of the touch points reaches a second preset distance, the recognizing unit recognizes all the gesture inputs that match the currently received trajectory of the touch input.

Preferably, the system further comprises a timing unit which starts timing from the beginning of the touch input. When a time calculated by the timing unit reaches a preset time, the recognizing unit recognizes all the gesture inputs that match the currently received trajectory of the touch input.

Compared with the existing technologies, one or more of the embodiments of the above technical solutions may have the following advantages or beneficial effects.

According to the method in the embodiments of the present disclosure, the system of the touch display device receives the trajectory of the touch input on the touch display device in real time, and then recognizes and displays all the gesture inputs that match the currently received trajectory of the touch input prior to the completion of the touch input, and finally receives the gesture input determined from all the gesture inputs, and executes a function corresponding to said gesture input. By this method, the system is able to predetermine gesture inputs possibly to be made by a user prior to the completion of the user's touch input, and enable a display unit to display all possible similar gesture inputs so as to provide an instruction (or navigation guidance) for the user. Thus, when using a large-sized touch display device, the user does not have to perform touch operations widely throughout the screen of the display device, because the system can recognize the similar gesture inputs in advance, which renders it easier for the user to operate on the touch display device, thereby obtaining a better user experience.

Other features and advantages of the present disclosure will be further explained in the following description, and will partly become self-evident therefrom, or be understood through the implementation of the present disclosure. The objectives and other advantages of the present disclosure will be achieved through the structures specifically pointed out in the description, claims, and the accompanying drawings.

BRIEF DESCRIPTION OF THE DRAWINGS

The accompanying drawings are provided for a further understanding of the present disclosure or the existing technologies, and constitute a part of the description. The drawings for the embodiments of the present disclosure, together with the embodiments of the present disclosure, are provided for illustrating the technical solutions of the present disclosure, rather than limiting the present disclosure.

DETAILED DESCRIPTION OF THE EMBODIMENTS

The present disclosure will be explained in detail below with reference to the embodiments and the accompanying drawings, so that one can fully understand how the present disclosure solves the technical problem and achieves the technical effects through the technical means, thereby implementing the same. It should be noted that as long as there is no structural conflict, any of the embodiments and any of the technical features thereof may be combined with one another, and the technical solutions obtained therefrom shall all fall within the scope of the present disclosure.

In addition, the steps as shown in the flow chart of the drawings can be carried out in a group of computer systems comprising executable computer instructions. A logic order has been given in the flow chart, but in some cases, the listed or described steps can also be carried out in different orders.

Figure 1:
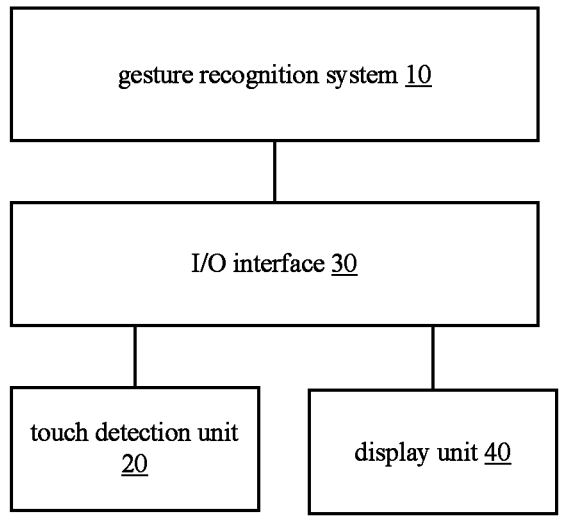
FIG. 1 schematically shows the structure of a touch display device according to an embodiment of the present disclosure.

FIG. 1 schematically shows a general structure of a touch display device provided in an embodiment of the present disclosure. It should be noted that the touch display device provided by the present disclosure can be used in televisions, personal computers, or mobile phones.

As shown in FIG. 1, the touch display device comprises a gesture recognition system 10, a touch detection unit 20, an I/O interface 30, and a display unit 40. The touch detection unit 20 is arranged on the display unit 40, and is used for detecting a user's touch input and then sending a detected trajectory of the touch input to the gesture recognition system 10 through the I/O interface 30. The gesture recognition system 10 receives the currently detected trajectory of the touch input from the touch detection unit 20 in real time, and recognizes all gesture inputs that can match the trajectory of the touch input prior to completion of the touch input. Then, the gesture recognition system 10 displays all the obtained gesture inputs on the display unit 40 by means of the I/O interface 30, and finally receives a gesture input determined by the user based on all the gesture inputs displayed on the display unit 40, and executes a function corresponding to said gesture input.

Figure 2:
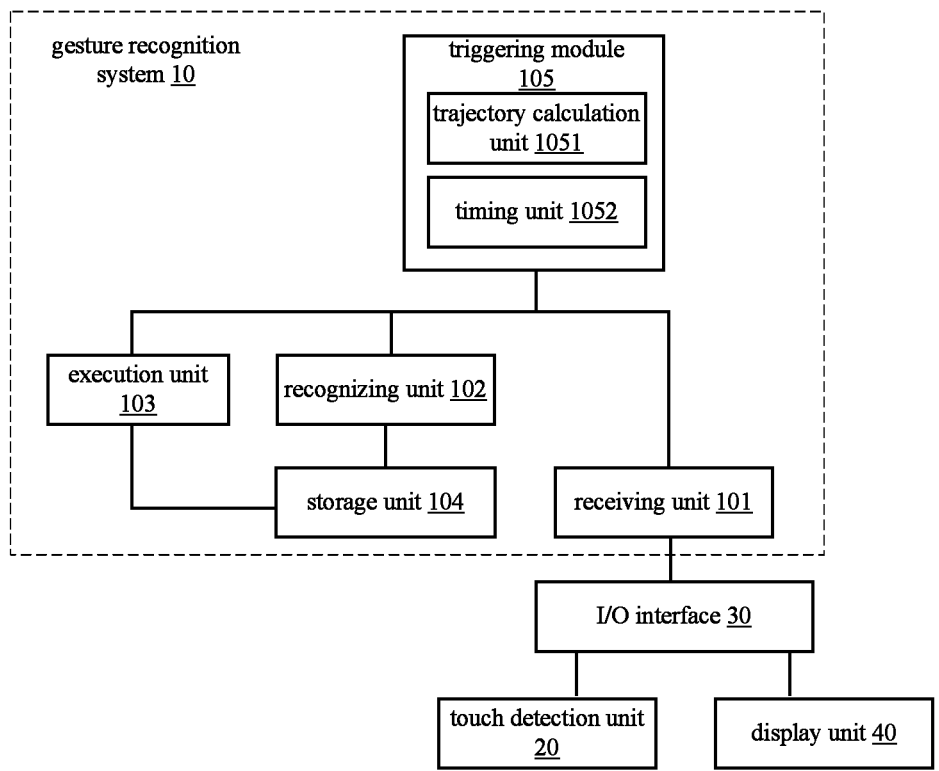
FIG. 2 schematically shows the structure of a system of gesture recognition in the touch display device according to the embodiment of the present disclosure.

As shown in FIG. 2, the gesture recognition system 10 mainly comprises a receiving unit 101, a recognizing unit 102, and an execution unit 103. The receiving unit 101 receives the trajectory of the touch input on the touch display device in real time through the I/O interface 30. The recognizing unit 102 recognizes all the gesture inputs that can match the currently received trajectory of the touch input prior to the completion of the touch input. The execution unit 103 receives the gesture input determined from all the gesture inputs displayed on the touch display device (or the display unit), and executes the function corresponding to said gesture input.

Figures 4A, 4B:
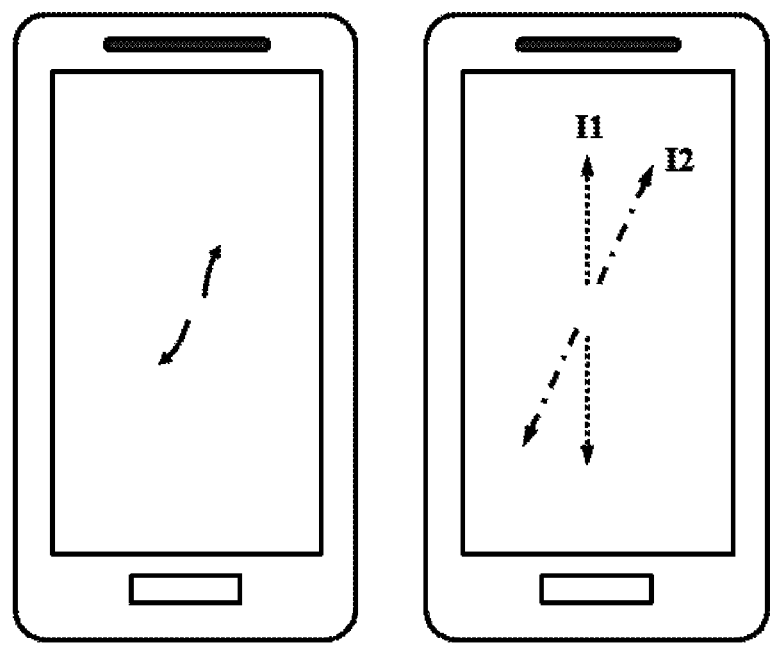
FIG. 4(a) and FIG. 4(b) are exemplary diagrams showing different phases of a gesture input on the touch display device.

In addition, the gesture recognition system 10 further comprises a storage unit 104 for storing information of various gesture inputs, especially of multi-point touch gesture inputs. This information is stored in accordance with the following lists, namely, the specific touch gesture and the corresponding input signal caused by the touch gesture (e.g., function signals achieving the operations of clicking, dragging, zooming in and out, and rotating). The storage unit 104 can be a memory of a television or a mobile phone, or a hard disk of a computer. The specific touch gestures may include single clicking, double clicking, as well as holding and dragging with one finger, or stretching in a direction perpendicular to or forming a forty-five degree angle to a direction of the operating window with two fingers as shown in FIG. 4.

To ensure that the recognizing unit 102 can recognize all the gesture inputs that match the currently received trajectory of the touch input prior to the completion of the touch input, the gesture recognition system 10 is further provided a triggering module 105 for triggering an action of the recognizing unit 102 at a certain time (a time prior to the completion of the touch input). As shown in FIG. 2, the triggering module 105 is connected to the recognizing unit 102, and comprises a trajectory calculation unit 1051 and/or a timing unit 1052. The trajectory calculation unit 1051 is able to calculate a real-time distance between two touch points of the touch input, and calculate distance variation of the trajectory of each of the touch points. The distance variation of the trajectory refers to the distance variation of the touch point from its initial position. The timing unit 1052 starts timing from the beginning of the touch input.

In this case, when the real-time distance between the two touch points calculated by the trajectory calculation unit 1051 reaches a first preset distance, or when the distance variation of the trajectory of at least one of the touch points reaches a second preset distance, or when the time calculated by the timing unit reaches a preset time, the recognizing unit 102 will be triggered to recognize all the gesture inputs that can match the currently received trajectory of the touch input, i.e., to start the recognition of the gesture inputs prior to the completion of the touch input.

When performing the recognition of the gesture inputs, the recognizing unit 102 first determines features of the trajectory of the touch input, and then selects all the gesture inputs having said features from a plurality of gesture inputs pre-stored in the storage unit 104. In the present embodiment, the features of the trajectory of the touch input include number of touch points, type of the trajectory, and quadrant where the trajectory is located. The present disclosure, however, is not restricted in this regard, and one skilled in the art may select other features as required.

Figure 3:
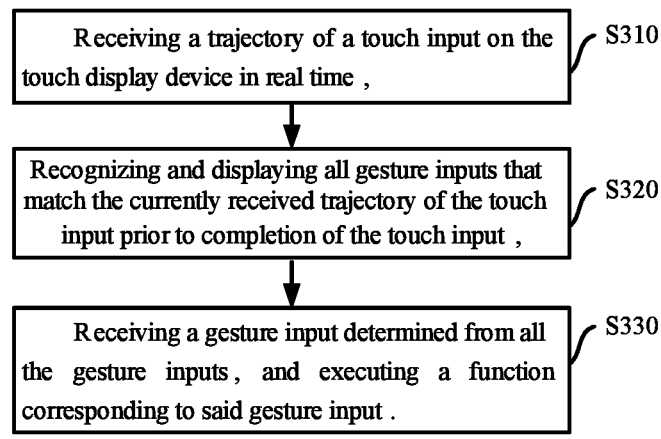
FIG. 3 schematically shows a flow chart of a method of gesture recognition in the touch display device according to the embodiment of the present disclosure.

FIG. 3 schematically shows a flow chart of the method of gesture recognition in the touch display device as provided in the present embodiment. The work flow of the gesture recognition system 10 will be illustrated below with reference to FIG. 2 and FIG. 3.

When the user performs a multi-point touch on the touch display device, the touch detection unit 20 detects the user's touch input in real time, and sends a detected trajectory of the touch input to the gesture recognition system 10 through the I/O interface 30. The receiving unit 101 receives the trajectory of the touch input on the touch display device in real time (Step S310).

As shown in FIG. 4(*a*), the user may perform a stretching input with two fingers on a large-sized display device. That is, the user may move his or her two fingers in opposite directions to achieve the function of zooming in a current operating window. When the user moves his or her fingers, the touch detection unit 20 detects positions of the fingers at a certain frequency (usually sixty times per second), and obtains the trajectory of the user's touch input by connecting the positions of the fingers at different times. After that, the detecting unit 20 sends the trajectory as shown in FIG. 4(*a*) to the receiving unit 101 through the I/O interface 30.

Then, the recognizing unit 102 recognizes all the gesture inputs that can match the currently received trajectory of the touch input prior to the completion of the user's touch input, and displays all the recognized gesture inputs on the display unit 40 through the receiving unit 101 and the I/O interface 30 (Step S320).

Specifically, taking the touch input as shown in FIG. 4(*a*) as an example, when the user performs a stretching operation on the large-sized display unit 40 with two fingers, and when the trajectory calculation unit 1051 detects that the real-time distance between the two touch points has reached the first preset distance (e.g., 5 cm), the recognizing unit 102 starts the recognition of the gesture inputs based on the currently received trajectory of the touch input. In this way, the user will, where possible, do not have to move widely throughout the large-sized display device when performing the operation of zooming in, and therefore gets less tired.

The recognizing unit 102 compares and matches the currently received trajectory of the touch input with the information of the various multi-point gesture inputs pre-stored in the storage unit 104.

In the following, FIG. 4 will be used as an example to illustrate how the recognizing unit 102 selects similar gesture inputs from the storage unit 104. First, the recognizing unit 102 determines the number of touch points of the trajectory of the touch input. In FIG. 4(*a*), the touch input is a two touch-point input. The recognizing unit 102 then selects all gesture inputs that are two touch-point inputs from the storage unit 104. After that, the recognizing unit 102 determines the type of the trajectory. In FIG. 4(*a*), the two fingers are performing a stretching action with relation to their initial positions. That is, with relation to their initial positions, both of the two fingers are moving toward the edges of the display device. Based on this, the recognizing unit 102 further selects, from gesture inputs that are two touch-point inputs, all gesture inputs in which both two touch points are stretched simultaneously. The recognizing unit 102 then determines the quadrant where the trajectory of the touch input is located. Supposing that a center of the initial positions of the two fingers is an original point, it can be determined that the one of the touch point moves in the first quadrant, while the other moves in the third quadrant, and that both the two touch points move away from the original point. The storage unit 104 stores two gesture inputs similar to the above movement (see FIG. 4(*b*)), one gesture input indicating a stretch in a perpendicular direction (a corresponding input signal is a signal that causes the operating window to maximize in a perpendicular direction), the other indicating a stretch in a forty-five degree direction (a corresponding input signal is a signal that causes the operating window to maximize in a forty-five degree direction). Thus, the recognizing unit 102 finally selects two gesture inputs similar to the trajectory of the touch input as shown in FIG. 4(*a*).

Subsequently, the display unit 40 displays all the recognized gesture inputs as a guidance, so as to indicate a possible similar gesture corresponding to the current touch input. As shown in FIG. 4(*b*), the display unit 40 displays a gesture I1 of a perpendicular stretch and a gesture I2 of a forty-five degree stretch.

Finally, the user selects a desired gesture input based on a plurality of the gesture inputs displayed on the display unit 40 of the touch display device, and clicks said desired gesture input. The touch detection unit 20 detects the click event, and sends this information to the receiving unit 101 through the I/O interface 30. The receiving unit 101 receives the gesture input determined from all the gesture inputs. Then, the execution unit 103 connected to the receiving unit 101 executes the function corresponding to said gesture input (Step S330).

After the user selects the gesture of perpendicular stretch I1 as shown in FIG. 4(*b*), the execution unit 103 achieves the maximization of the operating window in the perpendicular direction. And after the user selects the gesture of forty-five degree stretch I2, the execution unit 103 achieves the maximization of the operating window in the forty-five degree direction.

In addition, when the distance variation of the trajectory of the at least one of the touch points calculated by the trajectory calculation unit 1501 reaches the second preset distance, the recognizing unit 102 is triggered to recognize all the gesture inputs that can match the currently received trajectory of the touch input.

For example, supposing that the user is performing a touch input in which two touch points approaches to each other so that the current operating window can be minimized, when the distance variation of the trajectory of the at least one of the touch points calculated by the trajectory calculation unit 1501 reaches the second preset distance (e.g., 4 cm), the recognizing unit 102 will be triggered to recognize all the gesture inputs that can match the currently received trajectory of the touch input prior to the completion of the touch input by the user.

Or, when the time calculated by the timing unit 1502 from the beginning of the touch input reaches the preset time (e.g., 0.5 s), the recognizing unit 102 will also be triggered to recognize all the gesture inputs that can match the currently received trajectory of the touch input.

According to the above, the gesture recognition system provided by the present embodiment receives the trajectory of the touch input on the touch display device in real time, and then recognizes and displays all the gesture inputs that can match the currently received trajectory of the touch input prior to the completion of the touch input, and finally receives the gesture input determined from all the gesture inputs, and executes the function corresponding to said gesture input. By this method, the system is able to predetermine the gesture inputs possibly to be made by the user prior to the completion of the user's touch input, and enable the display unit to display all possible similar gesture inputs so as to provide an instruction (or navigation guidance) for the user. Thus, when using a large-sized touch display device, users do not have to perform touch operations widely throughout the screen of the display device, because the system can recognize the similar gesture inputs in advance, which renders it easier for the users to operate on the touch display device, thereby getting a better user experience.

One skilled person in the art should understand that each of the units or the steps in the present disclosure can be implemented by commonly used computing devices, and can be integrated into one computing device, or be distributed in a network consists of a number of computing devices. Optionally, these units or steps can be implemented by means of program codes executable by a computing device, and therefore can be stored in a storage unit so as to be executed by a computing device, or each of them can be manufactured into an integrated circuit module, or some of them can be manufactured into one integrated circuit module. The present disclosure is not limited to a particular combination of hardware and software.

The above embodiments are described only for a better understanding of the present disclosure, rather than restricting the present disclosure. Anyone skilled in the art can make amendments to the implementing forms or details without departing from the spirit and scope of the present disclosure. The scope of the present disclosure should still be subject to the scope defined in the claims.

One skilled person in the art should understand that all the steps or part of the steps of the methods provided in the above embodiments can be carried out by related hardware under the instruction of programs. Said programs can be stored in a readable storage medium of a computer, and can be executed to perform the above steps. The storage medium can be ROM/RAM, diskettes, optical discs, etc.

The invention claimed is:

1. A method of gesture recognition in a touch display device, comprising steps of:
   receiving a trajectory of a touch input on the touch display device in real time,
   recognizing and displaying all gesture inputs that match the currently received trajectory of the touch input prior to completion of the touch input, and
   receiving a gesture input determined from all the gesture inputs, and executing a function corresponding to said gesture input,
   wherein the step of recognizing all the gesture inputs that match the currently received trajectory of the touch input comprises:
   determining features of the trajectory of the touch input, and
   selecting all the gesture inputs having said features from a plurality of pre-stored gesture inputs,
   wherein the features of the trajectory of the touch input include number of touch points, type of the trajectory, and quadrant where the trajectory is located.

2. The method according to claim 1, wherein when a real-time distance between two touch points of the touch input reaches a first preset distance, all the gesture inputs that match the currently received trajectory of the touch input are recognized and displayed.

3. The method according to claim 1, wherein when distance variation of the trajectory of at least one of the touch points of the touch input reaches a second preset distance, all the gesture inputs that match the currently received trajectory of the touch input are recognized and displayed.

4. The method according to claim 1, wherein when a time calculated from the beginning of the touch input reaches a preset time, all the gesture inputs that match the currently received trajectory of the touch input are recognized and displayed.

5. A system of gesture recognition in a touch display device, comprising:
   a receiving unit, for receiving a trajectory of a touch input on the touch display device in real time,
   a recognizing unit, for recognizing all gesture inputs that match the currently received trajectory of the touch input prior to completion of the touch input, and
   an execution unit, for receiving a gesture input determined from all the gesture inputs displayed on the touch display device, and executing a function corresponding to said gesture input,
   wherein the recognizing unit is further used to determine features of the trajectory of the touch input, and select all the gesture inputs having said features from a plurality of pre-stored gesture inputs,
   wherein the features of the trajectory of the touch input include number of touch points, type of the trajectory, and quadrant where the trajectory is located.

6. The system according to claim 5, further comprising a trajectory calculation unit for calculating a real-time distance between two touch points of the touch input,
   wherein when the real-time distance between the two touch points calculated by the trajectory calculation unit reaches a first preset distance, the recognizing unit recognizes all the gesture inputs that match the currently received trajectory of the touch input.

7. The system according to claim 6, wherein the trajectory calculation unit is further used to calculate distance variation of the trajectory of at least one of the touch points of the touch input, and
   when the distance variation of the trajectory of the at least one of the touch points calculated by the trajectory calculation unit reaches a second preset distance, the recognizing unit recognizes all the gesture inputs that match the currently received trajectory of the touch input.

8. The system according to claim 5, further comprising a timing unit which starts timing from the beginning of the touch input,
   wherein when a time calculated by the timing unit reaches a preset time, the recognizing unit recognizes all the gesture inputs that match the currently received trajectory of the touch input.

* * * * *